United States Patent [19]

Horodysky et al.

[11] Patent Number: 4,549,976

[45] Date of Patent: Oct. 29, 1985

[54] LUBRICANT COMPOSITION CONTAINING REACTION PRODUCTS OF VICINAL DIOLS AND PHOSPHORUS OXYHALIDES

[75] Inventors: Andrew G. Horodysky, Cherry Hill; Phillip S. Landis, Woodbury, both of N.J.

[73] Assignee: Mobil Oil Corporation, New York, N.Y.

[21] Appl. No.: 539,498

[22] Filed: Oct. 6, 1983

[51] Int. Cl.$^4$ ............................................... C10M 1/44
[52] U.S. Cl. .................................. 252/49.8; 260/937; 260/974
[58] Field of Search ................ 252/49.8; 260/974, 937

[56] References Cited

U.S. PATENT DOCUMENTS

| | | | |
|---|---|---|---|
| 2,536,685 | 1/1951 | Harman et al. | 252/49.8 X |
| 2,661,366 | 12/1953 | Gamrath et al. | 260/974 X |
| 2,723,237 | 11/1955 | Ferrin | 252/49.8 |
| 2,856,369 | 10/1958 | Smith et al. | 252/49.8 X |
| 2,892,862 | 6/1959 | Lanham | 252/49.8 X |
| 2,978,478 | 4/1961 | Sandner et al. | 252/49.8 X |
| 3,005,007 | 10/1961 | Fierce et al. | 252/49.8 X |
| 3,021,354 | 2/1962 | Lanham | 260/974 X |
| 3,192,162 | 6/1965 | Bartlett et al. | 252/49.8 X |
| 3,965,220 | 6/1976 | Schumacher | 252/49.8 X |

*Primary Examiner*—Jacqueline V. Howard
*Attorney, Agent, or Firm*—Alexander J. McKillop; Michael G. Gilman; Van D. Harrison, Jr.

[57] ABSTRACT

Lubricants and liquid fuel compositions containing a phosphorus oxyhalide vicinal diol reaction product provide additional protection to metal parts in contact by reducing the amount of friction.

20 Claims, No Drawings

LUBRICANT COMPOSITION CONTAINING REACTION PRODUCTS OF VICINAL DIOLS AND PHOSPHORUS OXYHALIDES

BACKGROUND OF THE INVENTION

1. Field of the Invention

This invention relates to friction reducing additives for lubricants and liquid fuels. More particularly, the invention relates to lubricant and fuel compositions to which has been added a phosphorus-containing compound.

2. Discussion of the Prior Art

The metal surfaces of machinery or engines operating under heavy or normal loads wherein metal is under friction, undergo metal to metal contact even when being lubricated. Thus, there is always metal wear which can be excessive. Often lubricants used to protect the metal surfaces do not completely prevent wear at the points of metal to metal contact. Consequently, the performance of the machine or engine will suffer, and in aggravated cases the machine or engine may become completely inoperative from excessive wear caused the friction.

There have been many attempts to devise additive systems to improve the friction properties of a lubricant. The phosphate derivatives of the present invention are believed to be capable of overcoming some of the deficiencies of prior art additives and to provide lubricating oil compositions with enhanced friction characteristics.

U.S. Pat. No. 2,758,971 describes a class of metal phosphonates which are disclosed as having properties which prevent breakdown of oils at high temperatures.

U.S. Pat. No. 2,792,374 discloses the alkali metal salts of certain alkyl alkylphosphonic acids as defoamants in aqueous systems.

U.S. Pat. No. 4,356,097 teaches an engine crankcase lubricating oil containing a dihydrocarbyl hydrocarbyl-phosphonate, which oil exhibits reduced friction.

U.S. Pat. No. 2,982,727 discloses lubricating oil compositions containing certain salts of oxygen-containing esters of phosphorus. The esters are phosphonates similar to those described in U.S. Pat. No. 2,758,971.

U.S. Pat. No. 4,382,035 discloses a new glycerol-3-phosphoric acid halogenalkyl ester of the formula

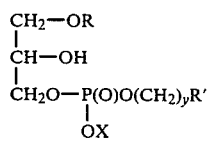

where R, R', X and y are as defined therein. Certain diols have been disclosed as having lubricity properties when formulated into lubricants and for their water-scavaging abilities in fuels. Phosphate esters are well known as functional lubricants.

However, no art is known that teaches or suggests the phosphate ester of the present invention.

SUMMARY OF THE INVENTION

In accordance with the invention, there are provided a product of reaction made by reacting a phosphorus oxyhalide, preferably the oxychloride, with a vicinal diol and a lubricant or liquid fuel composition comprising a major proportion of a lubricant or fuel and an antifriction amount of said product of reaction. The products also have fuel consumption reducing properties when used in internal combustion engines.

DESCRIPTION OF SPECIFIC EMBODIMENTS

Because of the relatively complex nature of the reaction that occurs when phosphorus oxyhalide and vicinal diols are interacted, no precise structure can be assigned to the product. Thus, the final product will be referred to herein, both in the specification and the claims, as the product of the specified reaction.

However, it is believed that the reaction product obtained by reacting the diol with, for example, POCl$_3$ comprises at least some of the following compounds:

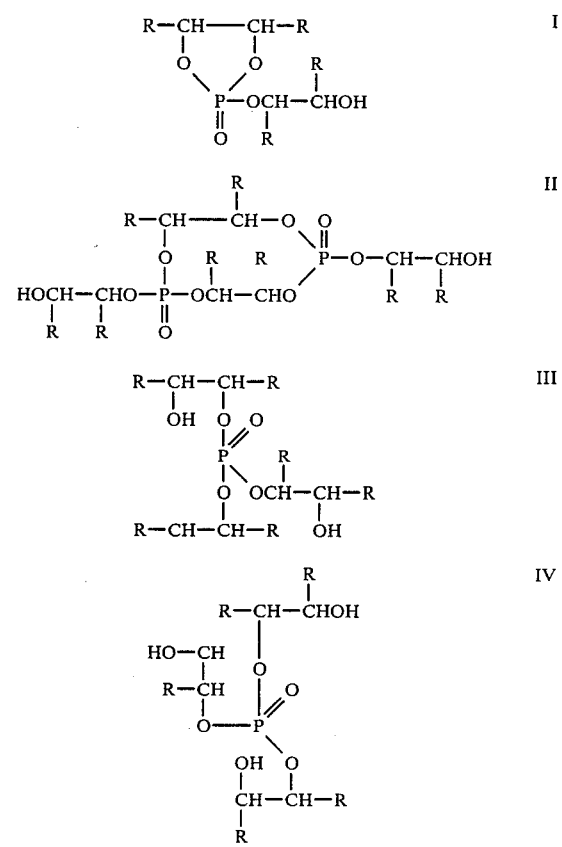

and oligomers thereof. R is as defined below.

It will be understood that these are only illustrations and that numerous other compounds, as the art will understand, are possible and that they are obtained using one equivalent of diol and up to one equivalent of phosphorus oxyhalide.

The hydrocarbyl vicinal diols contemplated for use in this invention are hydrocarbyl diols having vicinal hydroxy groups. They have the formula:

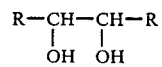

wherein R is hydrogen or a hydrocarbyl group containing 8 to 30 carbon atoms, preferably 12 to 18 carbon atoms, including mixtures thereof. At least one R is a hydrocarbyl group and can be linear or branched, saturated or unsaturated. The two hydroxy groups are preferably near the end of the hydrocarbyl chain. The hydrocarbyl groups are preferably alkyl groups, but may also be aryl, alkaryl, aralkyl, cycloalkyl groups.

Among the diols contemplated are 1,2-dodecanediol, 1,2-tetradecanediol, 1,2-pentadecanediol, 1,2-hexadecanediol, 1,2-heptadecanediol, 1,2-octadecanediol, mixed 1,2-$C_{15}$–$C_{18}$ alkanediols, and mixtures of all such diols, including mixtures of similar diols. Mixtures are often preferred.

The vicinal diols can be synthesized using several methods known to the art. One such method, described in an article in *J. Am. Chem. Soc.*, 68, 1504 (1946), involves the hydroxylation of 1-olefins with peracids. Vicinal diols can also be prepared by the peroxytrifluoroacetic acid method for the hydroxylation of olefins as described in *J. Am. Chem. Soc.*, 76, 3472 (1954). Similar procedures can be found in U.S. Pat. Nos. 2,411,762, 2,457,329 and 2,455,892. These are incorporated herein by reference.

The diols can also be prepared via catalytic epoxidation of an appropriate olefin, followed by hydrolysis.

As disclosed hereinabove, the preferred vicinal diols contain 12 to 18 carbon atoms. This range is preferred because diols having much less than 12 carbon atoms have significantly less friction reducing properties, while in those having more than 20 carbon atoms, solubility constraints or other adverse physical effects become significant. More preferred are the $C_{14}$ to $C_{18}$ hydrocarbyl groups and mixtures of such hydrocarbyl groups in which solubility, frictional characteristics and other properties appear to be maximized.

Other additives, such as detergents, dispersants, antioxidants, antiwear agents, extreme pressure additives, pour depressants, antirust additives and the like may be present in the composition. These may include phenates, sulfonates, succinimides, zinc dithiophosphates, polymers, calcium and magnesium containing additives and the like.

As mentioned hereinabove, the reactants may be used in equimolar quantities. That is, the reaction mixture may contain at least equivalent amounts of each reactant. Preferable, however are reaction mixtures containing diol and from about ¼ to about ½ of an equivalent amount thereof of phosphorus oxyhalide. In other words the best additive performance characteristics are obtained when the ratio of equivalents of diol: $POX_3$ is from about 4:1 to about 2:1. Preferably at least 5–10% and up to 75% of the hydroxy groups are reacted with phosphorus oxyhalide to form products containing from about 0.05% to about 10% phosphorus. Thus, some hydroxy groups on the diol remain unreacted in the preferred case.

The temperature of reaction will depend upon the reactants used. The temperature is not believed to be critical and the reaction can be run over a wide range of from about 60° C. to about 225° C., preferably from about 80° C. to about 150° C.

Times of reaction are not critical, but they will vary depending upon the size and complexity of the reactants and the reactant temperature. Under normal conditions, the reaction with the contemplated reactants can be completed in from about 1 hour to about 10 hours, preferably from about 1 hour to about 3 hours. A solvent is desirable in some cases where strongly exothermic reaction occurs and generally useful for the azeotropic removal of the water formed during the condensation reaction. Where a solvent is used, it should be one in which the products are soluble and which can be relatively easily removed. Examples of some solvents that may be useful solvents are toluene, benzene, xylene, cyclohexane, hexane and the like.

Atmospheric pressure can be used, but reduced pressure is often desirable as an aid to eliminate hydrogen chloride produced during the reaction.

The compounds of the invention are used with lubricating oils or greases to the extent of from about 0.1% to about 10% by weight of the total composition, and with fuels to the extent of from about 5 lbs. to about 250 lbs. per 1000 bbls. of fuel. Furthermore, other additives, such as detergents, antioxidants, antiwear agents and the like may be present. These can include phenates, sulfonates, succinimides, zinc dialkyl dithiophosphates, polymers, calcium and magnesium salts of phenates and sulfonates, including overbased salts of the same, and the like.

The lubricants contemplated for use with the esters herein disclosed include mineral and synthetic hydrocarbon oils of lubricating viscosity, mixtures of mineral oils and synthetic oils and greases from any of these, including the mixtures. The synthetic hydrocarbon oils include long-chain alkanes such as cetanes and olefin polymers such as oligomers of hexene, octene, decene, and dodecene, etc. These vicinal diols are especially effective in synthetic oils formulated using mixtures of synthetic hydrocarbon olefin oligomers and lesser amounts of hydrocarbyl carboxylate ester fluids. The other synthetic oils, which can be used alone with the borated compounds of this invention, or which can be mixed with a mineral or synthetic hydrocarbon oil, include (1) fully esterified ester oils, with no free hydroxyls, such as pentaerythritol esters of monocarboxylic acids having 2 to 20 carbon atoms, trimethylolpropane esters of monocarboxylic acids having 2 to 20 carbon atoms, (2) polyacetals and (3) siloxane fluids. Especially useful among the synthetic esters are those made from polycarboxylic acids and monohydric alcohols. More preferred are the ester fluids made by fully esterifying pentaerythritol, or mixtures thereof with di- and tripentaerythritol, with an aliphatic monocarboxylic acid containing from 1 to 20 carbon atoms, or mixtures of such acids.

A wide variety of thickening agents can be used in the greases of this invention. Included among the thickening agents are alkali and alkaline earth metal soaps of fatty acids and fatty materials having from about 12 to about 30 carbon atoms per molecule. The metals are typified by sodium, lithium, calcium and barium. Fatty materials are illustrated by stearic acid, hydroxystearic acid, stearin, cottonseed oil acids, oleic acid, palmitic acid, myristic acid and hydrogenated fish oils.

Other thickening agents include salt and salt-soap complexes as calcium stearate-acetate (U.S. Pat. No. 2,197,263), barium stearate acetate (U.S. Pat. No. 2,564,561), calcium stearate-caprylate-acetate complexes (U.S. Pat. No. 2,999,065), calcium caprylate-acetate (U.S. Pat. No. 2,999,066), and calcium salts and soaps of low-, intermediate- and high-molecular weight acids and of nut oil acids.

Another group of thickening agents comprises substituted ureas, phthalocyanines, indanthrene, pigments such as perylimides, pyromellitdiimides, and ammeline.

The preferred thickening gelling agents employed in the grease compositions are essentially hydrophobic clays. Such thickening agents can be prepared from clays which are initially hydrophilic in character, but which have been converted into a hydrophobic condition by the introduction of long chain hydrocarbon radicals onto the surface of the clay particles prior to their use as a component of a grease composition, as, for example, by being subjected to a preliminary treatment with an organic cationic surface active agent, such as an onium compound. Typical onium compounds are tetraalkylammonium chlorides, such as dimethyl dioctadecyl ammonium chloride, dimethyl dibenzyl ammonium chloride and mixtures thereof. This method of conversion, being well known to those skilled in the art, is believed to require no further discussion, and does not form a part of the present invention. More specifically, the clays which are useful as starting materials in forming the thickening agents to be employed in the grease compositions, can comprise the naturally occurring chemically unmodified clays. These clays are crystalline complex silicates, the exact composition of which is not subject to precise description, since they vary widely from one natural source to another. These clays can be described as complex inorganic silicates such as aluminum silicates, magnesium silicates, barium silicates, and the like, containing, in addition to the silicate lattice, varying amounts of cation-exchangeable groups such as sodium. Hydrophilic clays which are particularly useful for conversion to desired thickening agents include montmorillonite clays, such as bentonite, attapulgite, hectorite, illite, saponite, sepiolite, biotite, vermiculite, zeolite clays, and the like. The thickening agent is employed in an amount from about 0.5 to about 30, and preferably from 3 percent to 15 percent by weight of the total grease composition.

The liquid fuels contemplated include the liquid hydrocarbons, such as gasoline, fuel oil and diesel oil and the liquid alcohols such as methyl alcohol and ethyl alcohol. The fuels also include mixtures of alcohols as well as mixtures of alcohols and liquid hydrocarbons.

Having described the invention in general aspects, the following Examples are offered as specific illustrations. Parts are by weight.

EXAMPLE 1

Phosphate Ester of 1,2-Mixed Pentadecanediol-Octadecanediol

Approximately 240 g of 1,2-mixed pentadecanediol-octadecanediol (obtained as Vikol 158 from Viking Chemical Co. and containing by weight about 28% 1,2-pentadecanediol, 28% 1,2-hexadecanediol, 28% 1,2-heptadecanediol and 16% 1,2-octadecanediol) was heated to about 60° C. in a glass reactor equipped with agitator and provision for reducing the pressure to 1/10 atmosphere. Over a period of ~1 hour, 35 g of phosphorus oxychloride (POCl$_3$) were added dropwise while maintaining a temperature of 70°–75° C., and reduced pressure. The reaction mixture was then held at 85°–90° C. for 6 additional hours at reduced pressure until evolution of hydrogen chloride ceased. The product was pale amber fluid which became waxy upon cooling.

EXAMPLE 2

Phosphate Ester of 1,2-Mixed Pentadecanediol-Octadecanediol

Approximately 240 g of 1,2-mixed pentadecanediol-octadecanediol (Vikol) 158 of Example 1) were heated to 60° C. in a glass reactor equipped with agitator and provision for reducing the pressure to 1/10 atoms. Over a period of 1 hour, 52 g of phosphorus oxychloride were added dropwise while maintaining a temperature of 68°–70° C. at reduced pressure. The reaction mixture was then held at 80° C. for seven additional hours at reduced pressure until evolution of hydrogen chloride ceased. The product was a pale amber fluid which became waxy on cooling.

EXAMPLE 3

Phosphate Ester of 1,2-Mixed Pentadecanediol-Octadecanediol

Approximately 240 g of 1,2-mixed pentadecanediol-octadecanediol (Vikol 158 of Examples 1 and 2) were heated to 65° C. in a glass reactor equipped with agitator and provision for reducing the pressure to 1/10 atmosphere. Over a period of 1 hour, 23 g of phosphorus oxychloride were added dropwise while maintaining a temperature of 65°–70° C. at reduced pressure. The reaction mixture was then held at 90°–95° C. for seven additional hours at reduced pressure until evolution of hydrogen chloride ceased. The product was a pale amber fluid which became waxy on cooling.

EXAMPLE 4

Phosphate Ester of 1,2-Dodecanediol

Approximately 278 g of 1,2-dodecanediol (obtained as Vikol 12 from Vicking Chemical Company) were heated to 60° C. in a glass reactor equipped as in Example 3. Over a period of about 1 hour, 76 g of phosphorus oxychloride were added dropwise at reduced pressure while maintaining 65°–75° C. The reaction mixture was then held at about 105° C. for 5 additional hours at reduced pressure until evolution of hydrogen chloride ceased.

EVALUATION OF PRODUCTS

The phosphorus esters of hydrocarbyl diols were blended into fully formulated synthetic and mineral oil based automotive engine oil lubricants and evaluated using the Low Viscosity Friction Apparatus Test. As shown in Table 1 the use of only 1% of the product of Example 1 reduced the coefficient of friction by 44%.

LOW VELOCITY FRICTION APPARATUS

Description

The Low Velocity Friction Apparatus (LVFA) is used to measure the friction of test lubricants under various loads, temperatures, and sliding speeds. The LVFA consists of a flat SAE 1020 steel surface (diam. 1.5 in.) which is attached to a drive shaft and rotated over a stationary, raised, narrow ringed SAE 1020 steel surface (area 0.08 in.$^2$). Both surfaces are submerged in the test lubricant. Friction between the steel surfaces is measured as a function of the sliding speed at a lubricant temperature of 250° F. The friction between the rubbing surfaces is measured using a torque arm-strain gauge system. The strain gauge output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½ HP electric motor. To vary the sliding speed, the output speed of the transmission is regulated by a lever-cam motor arrangement.

Procedure

The rubbing surfaces and 12-13 ml of test lubricant are placed on the LVFA. A 240 psi load is applied, and the sliding speed is maintained at 40 fpm at ambient temperature for a few minutes. A plot of coefficients of friction ($U_k$) over the range of sliding speeds, 5 to 40 fpm (25-195 rpm), is obtained. A minimum of three measurements is obtained for each test lubricant. Then, the test lubricant and specimens are heated to 250° F., another set of measurements is obtained, and the system is run for 50 minutes at 250° F., 240 psi and 40 fpm sliding speed. Afterward, measurements of $U_k$ vs. speed are taken at 240, 300, 400, and 500 psi. Freshly polished steel specimens are used for each run. The surface of the steel is parallel ground to 4-8 microinches.

The results obtained are shown in Tables 1 and 2. The data in the tables are reported as percent reduction in coefficient of friction at two speeds. The friction-reducing ester additives were evaluated in a fully formulated mineral lubricating oil (Table 1) or 5W-30 synthetic lubricating oil (Table 2), each comprising an additive package including antioxidant, detergent and dispersant.

TABLE 1

Friction Test Results Using Low Velocity Friction Apparatus

| | Additive Conc. in Base Fluid Weight % | % Reduction in Coefficient of Friction at | |
|---|---|---|---|
| | | 5 Ft/Min | 30 Ft/Min |
| Base Fluid (fully formulated mineral oil based automotive engine oil containing detergent/dispersant/inhibitor performance package) SAE 10W40 | — | 0 | 0 |
| Example 1 Plus Base Fluid | 0.5 | 27 | 34 |
| | 1 | 44 | 29 |
| Example 2 Plus Base Fluid | 1 | 41 | 24 |
| Example 3 Plus Base Fluid | 1 | 52 | 41 |
| Example 4 Plus Base Fluid | 1 | 21 | 11 |

TABLE 2

Friction Test Results Using Low Velocity Friction Apparatus

| | Additive Conc. in Base Fluid Weight % | % Reduction in Coefficient of Friction at | |
|---|---|---|---|
| | | 5 Ft/Min | 30 Ft/Min |
| Base Fluid (fully formulated synthetic oil based automotive engine oil containing detergent/dispersant/inhibitor performance package) SAE 5W30 | — | 0 | 0 |
| Example 1 Plus Base Fluid | 1 | 42 | 39 |
| Example 2 Plus Base Fluid | 0.5 | 22 | 17 |
| Example 3 Plus Base Fluid | 1 | 37 | 38 |

We claim:

1. A product of reaction obtained by reacting (1) a mixture of hydrocarbyl vicinal diols of the formula

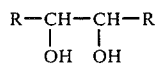

wherein R is hydrogen or a hydrocarbyl group containing 12 to 18 carbon atoms, at least one R being a hydrocarbyl group, with (2) a phosphorus oxyhalide said reaction being carried out at a temperature between about 60° C. and about 225° C., and a mole ratio of diol to phosphorus oxyhalide of between about 4:1 and about 2:1.

2. The product of claim 1 wherein the hydrocarbyl group is an alkyl, aryl, aralkyl, alkaryl or cycloalkyl group.

3. The product of claim 2 wherein the hydrocarbyl group is an alkyl group.

4. The product of claim 1 wherein one R is hydrogen and the other R is a decyl, dodecyl, tridecyl, tetradecyl, pentadecyl, hexadecyl, mixed $C_{13}$–$C_{16}$ alkyl group or mixtures of such groups.

5. The product of claim 1 wherein the phosphorus oxyhalide is phosphorus oxychloride.

6. The product of claim 1 wherein the vicinal diol is 1,2-mixed pentadecanediol-octadecanediol and the phosphorus oxyhalide is phosphorus oxychloride.

7. The product of claim 1 wherein the mixture of diols contains about 28% 1,2-pentadecanediol, about 28% 1,2-hexadecanediol, about 28% 1,2-heptadecanediol and about 16% 1,2-octadecanediol.

8. A lubricant composition comprising a major proportion of lubricant and an antifriction amount of product of reaction obtained by reacting (1) a mixture of hydrocarbyl vicinal diols of the formula

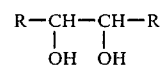

wherein R is hydrogen or a hydrocarbyl group containing 12 to 18 carbon atoms, at least one R being a hydrocarbyl group, with (2) a phosphorus oxyhalide.

9. The composition of claim 8 wherein the hydrocarbyl group is an alkyl, aryl, aralkyl, alkaryl or cycloalkyl group.

10. The composition of claim 8 wherein the hydrocarbyl group is an alkyl group.

11. The composition of claim 8 wherein one R is hydrogen and the other R is a decyl, dodecyl, tridecyl, tetradecyl, pentadecyl, hexadecyl, mixed $C_{13}$–$C_{16}$ alkyl group or mixtures of such groups.

12. The composition of claim 8 wherein the phosphorus oxyhalide is phosphorus oxychloride.

13. The composition of claim 8 wherein the vicinal diol is 1,2-mixed pentadecanediol-octadecanediol and the phosphorus oxyhalide is phosphorus oxychloride.

14. The composition of claim 8 wherein the mixture of diols contains about 28% 1,2-pentadecanediol, about 28% 1,2-hexadecanediol, about 28% 1,2-heptadecanediol and about 16% 1,2-octadecanediol.

15. The composition of claim 8 wherein the lubricant is (1) a mineral oil, (2) a synthetic oil or mixture of synthetic oils, (3) a mixture of (1) and (2) or a grease of (1), (2) or (3).

16. The composition of claim 15 wherein the lubricant is a mineral oil.

17. The composition of claim 15 wherein the lubricant is a synthetic oil or mixture of synthetic oils.

18. The composition of claim 15 wherein the lubricant is said mixture of (1) and (2).

19. The composition of claim 15 wherein the lubricant is said grease.

20. A method of reducing fuel consumption in an internal combustion engine by lubricating said engine with a composition comprising a major proportion of a lubricant and a fuel consumption reducing amount of product of reaction obtained by reacting (1) a hydrocarbyl vicinal diol mixture of the formula $$R-CH(OH)-CH(OH)-R$$

wherein R is hydrogen or a hydrocarbyl group containing 12 to 18 carbon atoms, at least one R being a hydrocarbyl group, with (2) a phosphorus oxyhalide.

* * * * *